United States Patent [19]
Soppet et al.

[11] Patent Number: 5,958,729
[45] Date of Patent: Sep. 28, 1999

[54] HUMAN G-PROTEIN RECEPTOR HCEGH45

[75] Inventors: Daniel R. Soppet, Centreville, Va.; Yi Li, Sunnyvale, Calif.; Craig A. Rosen, Laytonsville; Steven M. Ruben, Olney, both of Md.

[73] Assignee: Human Genome Sciences, Inc., Rockville, Md.

[21] Appl. No.: 08/982,412

[22] Filed: Dec. 2, 1997

Related U.S. Application Data

[63] Continuation of application No. 08/465,976, Jun. 6, 1995, Pat. No. 5,869,632.

[60] Provisional application No. 60/032,186, Dec. 2, 1996.

[51] Int. Cl.⁶ ............................... C12N 5/10; C12N 15/12
[52] U.S. Cl. .................. 435/69.1; 435/252.3; 435/320.1; 536/23.5; 536/24.31
[58] Field of Search ..................................... 530/350, 324; 435/69.1, 69.7; 536/23.4, 23.5, 24.31

[56] References Cited

U.S. PATENT DOCUMENTS 5,328,838  7/1994  Galli et al. .
5,366,889  11/1994  McDonald et al. .

FOREIGN PATENT DOCUMENTS

0618291 A2  10/1994  European Pat. Off. .
WO94/11504  5/1994  WIPO .
WO96/16087  5/1996  WIPO .
WO96/39439  12/1996  WIPO .

OTHER PUBLICATIONS

Bischoff et al., EP Journal of Immunology, vol. 23:761–767 (1993).
Iismaa, T.P. et al., Genomics 24: 391–394 (1994).
Schweickart, V.L. et al., Genomics 23: 643–650 (1994).
Heiber, M. et al., DNA and Cell Biology 14: 25–35 (1995).
Hata, S. et al., Biochimica et Biophysica Acta 1261: 121–125 (1995).
Marchese, A. et al., Biochemical & Biophysical Research Comm., 205: 1952–1958 (1994).
Marchese, A. et al., Genomics 23: 609–618 (1994).
Database EMBL Nucleotide Sequences Accession No. N95759 & W24853 (1996).
Ross, P. C. et al., Proc. Natl. Acad. Sci., 87: 3052–3056 (1990).
Libert, F. et al., Science 244: 569–572 (1989).
Eva, C. et al., FEBS 271:81–84 (1990).
Hla, T. et al., J. of Biol. Chem., 265: 9308–9313 (1990).
Meyerhof, W. et al., FEBS 284: 155–160 (1991).
Scott, J.K., et al., Science 249: 386–249 (1990).
Nagase, T., et al., DNA Research 3: 321–329 (1996).

*Primary Examiner*—John Ulm
*Attorney, Agent, or Firm*—A. Anders Brookes

[57] ABSTRACT

A human G-protein receptor HCEGH45 polypeptide and DNA (RNA) encoding such polypeptide and a procedure for producing such polypeptide by recombinant techniques is disclosed. Also disclosed are methods for utilizing such polypeptide for identifying antagonists and agonists to such polypeptide. Antagonists against such polypeptides may be used therapeutically to treat PACAP hypersecretory conditions and to create pharmacological amnesia models while the agonists may be employed to treat amnesia and Alzheimer's disease. Also disclosed are diagnostic methods for detecting a mutation in the receptor nucleic acid sequences and detecting a level of the soluble form of the receptors in a sample derived from a host.

28 Claims, 6 Drawing Sheets

Nucleotide Sequence and predicted protein for HCEGH45

```
              10                    30                    50
-210 GTCCCCACGGCCATCCCCATCTAAGGTCCTGCCCACAAGCAGCAGCATAGAAAACTCCAC    -151
              70                    90                   110
-150 CACCTCAAGTGTGGTCCCCCCACCAGCCCCGCCAGAGCCAGAGCCTGGGATCTCCATTAT     -91
             130                   150                   170
 -90 AATTCTCCTCGTTTACCGCACCTTAGGGGGACTGCTCCCTGCCCAGTTCCAGGCAGAACG     -31
             190                   210                   230
 -30 CCGAGGTGCCAGGCTTCCTCAGAACCCCGTCATGAACTCCCCGGTGGTCAGCGTGGCTGT      29
  -9                                  M  N  S  P  V  V  S  V  A  V   10

250                   270                   290
  30 GTTCCACGGACGCAACTTCCTAAGGGGAATCCTGGAGTCCCCCATCAGCCTAGAGTTTCG      89
  11  F  H  G  R  N  F  L  R  G  I  L  E  S  P  I  S  L  E  F  R     30

310                   330                   360
  90 CCTGCTACAGACAGCGAATCGGAGCAAGGCGATCTGTGTGCAGTGGGACCCACCTGGCCT     149
  31  L  L  Q  T  A  N  R  S  K  A  I  C  V  Q  W  D  P  P  G  L     50

370                   390                   410
 150 GGCGGAGCAGCATGGTGTGTGGACAGCACGGGACTGCGAGCTGGTGCACAGGAATGGGTC     209
  51  A  E  Q  H  G  V  W  T  A  R  D  C  E  L  V  H  R  N  G  S     70

430                   450                   470
 210 CCACGCACGGTGTCGCTGCAGCCGGACAGGGACCTTTGGGGTCCTCATGGATGCCTCTCC     269
  71  H  A  R  C  R  C  S  R  T  G  T  F  G  V  L  M  D  A  S  P     90

490                   510                   530
 270 CCGTGAGAGGCTGGAGGGCGACCTGGAGCTGCTGGCTGTGTTCACCCACGTGGTCGTGGC     329
  91  R  E  R  L  E  G  D  L  E  L  L  A  V  F  T  H  V  V  V  A    110

550                   570                   590
 330 TGTGTCTGTGGCTGCGCTGGTCTGACTGCAGCCATCCTGCTGAGCCTGCGCAGCCTCAA     389
 111  V  S  V  A  A  L  V  L  T  A  A  I  L  L  S  L  R  S  L  K    130

610                   630                   650
 390 GTCCAATGTGCGTGGGATCCATGCCAATGTGGCAGCCGCCCTGGGGGTGGCAGAGCTCCT     489
 131  S  N  V  R  G  I  H  A  N  V  A  A  A  L  G  V  A  E  L  L    150

670                   690                   710
 450 CTTCCTGCTGGGGATTCACAGGACCCACAATCAGCTGGTGTGCACTGCAGTCGCCATCCT     509
 151  F  L  L  G  I  H  R  T  H  N  Q  L  V  C  T  A  V  A  I  L    170

730                   750                   770
 510 CCTGCACTACTTCTTCCTCAGCACCTTCGCGTGGCTCTTCGTGCAGGGGCTGCACCTCTA     569
 171  L  H  Y  F  F  L  S  T  F  A  W  L  F  V  Q  G  L  H  L  Y    190

790                   810                   830
 570 CCGCATGCAGGTTGAGCCACGCAACGTGGACCGCGGCGCCATGCGCTTCTACCATGCCCT     629
 191  R  M  Q  V  E  P  R  N  V  D  R  G  A  M  R  F  Y  H  A  L    210

850                   870                   890
 630 GGGCTGGGGCGTCCCTGCTGTGCTGCTGGGCCTTGCTGTGGGCCTGGACCCTGAGGGCTA     689
 211  G  W  G  V  P  A  V  L  L  G  L  A  V  G  L  D  P  E  G  Y    230

910                   930                   950
 690 TGGGAACCCTGACTTCTGCTGGATCTCAGTCCACGAGCCCCTCATCTGGAGCTTTGCTGG     749
 231  G  N  P  D  F  C  W  I  S  V  H  E  P  L  I  W  S  F  A  G    250
```

FIG.1A

```
            970                990               1010
 750 CCCTGTTGTCCTGGTCATAGTGATGAACGGGACCATGTTTCTCCTCGCTGCCCGCACATC    809
 251  P  V  V  L  V  I  V  M  N  G  T  M  F  L  L  A  A  R  T  S    270

1030               1050              1070
 810 CTGCTCCACAGGGCAGAGGGAGGCCAAGAAGACCTCTGCACTGACCCTTCGCAGCTCCTT    869
 271  C  S  T  G  Q  R  E  A  K  K  T  S  A  L  T  L  R  S  S  F    290

1090               1110              1130
 870 CCTGCTGCTTCTGCTGGTCAGTGCCTCCTGGCTCTTTGGGCTCCTGGCAGTCAACCACAG    929
 291  L  L  L  L  L  V  S  A  S  W  L  F  G  L  L  A  V  N  H  S    310

1150               1170              1190
 930 CATCCTAGCCTTCCACTACCTCCATGCTGGACTCTGCGGCCTCCAGGGCCTGGCGGTGCT    989
 311  I  L  A  F  H  Y  L  H  A  G  L  C  G  L  Q  G  L  A  V  L    330

1210               1230              1250
 990 GCTGCTCTTCTGTGTCCTAAATGCAGATGCTCGGGCTGCCTGGATGCCAGCCTGTCTGGG   1049
 331  L  N  F  C  V  L  N  A  D  A  R  A  A  W  M  P  A  C  L  G    350

1270               1290              1310
1050 CAGGAAGGCAGCGCCTGAGGAGGCAAGGCCAGCACCTGGGCTGGGACCTGGGGCCTACAA   1109
 361  R  K  A  A  P  E  E  A  R  P  A  P  G  L  G  P  G  A  Y  N    370

1330               1350              1370
1110 CAACACGGCTCTCTTTGAGGAGAGTGGCCTCATCCGCATCACTCTGGGCGCCTCCACCGT   1169
 371  N  T  A  L  F  E  E  S  G  L  I  R  I  T  L  G  A  S  T  V    390

1390               1410              1430
1170 CTCCTCTGTGAGCAGTGCCCGCTCCGGCCGGACCCAGGACCAGGACAGCCAGCGGGGCCG   1229
 391  S  S  V  S  S  A  R  S  G  R  T  Q  D  Q  D  S  Q  R  G  R    410

1450               1470              1490
1230 CAGCTACCTCAGGGACAATGTCCTGGTTCGACATGGCTCAGCCGCTGACCACACTGACCA   1289
 411  S  Y  L  R  D  N  V  L  V  R  H  G  S  A  A  D  H  T  D  H 1510               1530              1550
1290 CAGCCTCCAGGCTCATGCTGGCCCCACTGACCTGGACGTGGCCATGTTCCATCGAGATGC   1349
 431  S  L  Q  A  H  A  G  P  T  D  L  D  V  A  M  F  H  R  D  A    450

1570               1590              1610
1350 TGGCGCAGACTCCGACTCTGACAGTGACCTGTCCTTGGAGGAGGAGAGGAGTCTCTCCAT   1409
 451  G  A  D  S  D  S  D  S  D  L  S  L  E  E  E  R  S  L  S  I    470

1630               1650              1670
1410 TCCATCTTCAGAAAGCGAGGACAATGGCCGGACGCGGGGGCGCTTCCAACGGCCACTCTG   1469
 471  P  S  S  E  S  E  D  N  G  R  T  R  G  R  F  Q  R  P  L  C    490

1690               1710              1730
1470 CCGAGCAGCCCAGAGTGAGAGGCTCCTCACCCACCCCAAAGATGTGGATGGCAATGACCT   1529
 491  R  A  A  Q  S  E  R  L  L  T  H  P  K  D  V  D  G  N  D  L    510

1810               1830              1850
1590 GGGCTCTGAAAGGCGCCTGGGGCTGGACACCAGCAAGGATGCAGCTAACAACAACCAGCC   1649
 531  G  S  E  R  R  L  G  L  D  T  S  K  D  A  A  N  N  N  Q  P    550

1870               1890              1910
1650 AGACCCGGCCCTGACCAGTGGGGATGAGACTTCTCTGGGCCGGGCCCAGCGCCAGAGGAA   1709
 551  D  P  A  L  T  S  G  D  E  T  S  L  G  R  A  Q  R  Q  R  K    570
```

FIG. 1B

```
       1930              1950              1970
1710 AGGCATCCTGAAGAACCGGTTGCAATACCCACTGGTGCCACAGACCCGAGGTGCCCCTGA   1769
 571   G  I  L  K  N  R  L  Q  Y  P  L  V  P  Q  T  R  G  A  P  E   590

1990              2010              2030
1770 GCTGTCCTGGTGCCGTGCAGCCACCTTGGGCCACCGTGCTGTGCCAGCTGCCTCTTACGG   1829
 591   L  S  W  C  R  A  A  T  L  G  H  R  A  V  P  A  A  S  Y  G   610

2050              2070              2090
1830 TCGCATCTATGCTGGCGGGGGCACGGGCAGCCTTTCACAGCCAGCCAGCCGCTACTCTTC   1889
 611   R  I  Y  A  G  G  G  T  G  S  L  S  Q  P  A  S  R  Y  S  S   630

2110              2130              2150
1890 TAGAGAACAGCTGGACCTGCTCCTCCGGCGGCAACTGAGCCGTGAGCGACTAGAGGAAGC   1940
 631   R  E  Q  L  D  L  L  L  R  R  Q  L  S  R  E  R  L  E  E  A   650

2170              2190              2210
1950 CCCTGCCCCTGTTCTACGTCCCCTGAGCCGGCCAGGGTCCCAGGAATGCATGGATGCTGC   2009
 651   P  A  P  V  L  R  P  L  S  R  P  G  S  Q  E  C  M  D  A  A   670

2230              2250              2270
2010 ACCAGGCCGACTGGAGCCCAAAGATCGGGGCAGCACCCTGCCACGGAGGCAGCCACCTCG   2069
 671   P  G  R  L  E  P  K  D  R  G  S  T  L  P  R  R  Q  P  P  R   690

2290              2310              2330
2070 GGACTACCCTGGCGCCATGGCTGGCCGCTTCGGGTCACGGGATGCGCTCGACTTAGGGGC   2129
 691   D  Y  P  G  A  M  A  G  R  F  G  S  R  D  A  L  D  L  G  A   710

2350              2370              2390
2130 ACCTCGAGAGTGGTTGAGCACGCTGCCTCCGCCCCGCCGCACCCGGGACCTTGACCACAG   2189
 711   P  R  E  W  L  S  T  L  P  P  P  R  R  T  R  D  L  D  H  S   730

2410              2430              2450
2190 CCCCCACCTCTGCCCCTGTCTCCCCAGCGGCAACTCTCAAGGGACCCCCTCTTGCCATCC   2249
 731   P  H  L  C  P  C  L  P  S  G  N  S  Q  G  T  P  S  C  H  P   750

2470              2490              2510
2250 CGGCCGCTGGACTCTCTGTCTAGGAGCTCGAACTCTCGGGAGCAGCTGGACCAGGTGCCT   2309
 751   G  R  W  T  L  C  L  G  A  R  T  L  G  S  S  W  T  R  C  L   770

2530              2550              2570
2310 AGCCGGCACCCCTCACGAGAAGCCCTTGGGCCACTCCCGCAGCTGCTCAGAGCTAGGGAG   2369
 771   A  G  T  P  H  E  K  P  L  G  H  S  R  S  C  S  E  L  G  R   790

2590              2610              2630
2370 GACTCGGTCAGTGGCCCCAGCCATGGCCCCTCCACAGAACAGTTGGACATTCTTTCCTCC   2429
 791   T  R  S  V  A  P  A  M  A  P  P  Q  N  S  W  T  F  F  P  P   810

2650              2670              2690
2430 ATCCTTGCCTCTTTCAACTCCTCGGCCCTCTCCTCTGTGCAATCTTCAAGCACACCCTTG   2489
 811   S  L  P  L  S  T  P  R  P  S  P  L  C  N  L  Q  A  H  P  W   830

2710              2730              2750
2490 GGCCCTCACACCACTGCCACACCTTCTGCCACAGCCTCTGTGCTTGGGCCCTCCACGCCA   2549
 831   A  L  T  P  L  P  H  L  L  P  Q  P  L  C  L  G  P  P  R  H   850

2770              2790              2810
2550 CGTTCTGCCACGTCTCACAGCATCTCGGAGCTGTCGCCAGACTCAGAAGTTCCCAGAAGT   2609
 851   V  L  P  R  L  T  A  S  R  S  C  R  Q  T  Q  K  F  P  E  V   870

2830              2850              2870
2610 GAGGGTCACTCCTGAGGGGATGACGGCGTGGACGAGGAACAGCTGAGGGCGACAGAGGAT   2669
 871   R  V  T  P  E  G  M  T  A  W  T  R  N  S  *                  890
```

FIG.1C

```
             2890          2910           2930
2670 CTAGGCTAACAGGAGAGACTCCAGGAGTGGGGGCAGATCCCAAGGCAGCCTCCTGCTCCC    2729
             2950          2970           2990
2730 CAGTGGTGGGTGCCCCAGCTCTACCTGGTGTGGCAGGGCTGAGGCTCCATGTGCATCTGT    2789
             3010          3030           3050
2790 GAGCATGCGTGTGACAGGTGCAGAGACGGGGGACTGGAGGGAGACTTTTATACGTTTTGT    2849
             3070          3090           3110
2850 ACCTTTGTAACCAGAGAGATGCTTATGTTATTTTTCAGCTTTTCTGTCTCCTGGGGGGTT    2909
             3130          3150           3170
2910 TGAGCCTGGCTGGGAGGGGGAGGGAGATAGAGGGAGAGATGCAGTTTGACCCCATTTGGG    2960
             3190          3210           3130
2970 TCCTGAGCAAACCCTATGCTCATCTCTCTCCTTCCTGGGGTGGACTCAGATGGGTGGG     3029
             3250          3270           3290
3030 ACACATGCCTTCCTCCCCCTATTCCACCCCCAAGTTGATCTGAGTATCGTCAGGGGCCCA    3089
             3310          3330           3350
3090 AGTACAGAATTGTTCTTTGCTTTTTATTGAATGCTCCAAAGGCCAAACTTCTGGGGCTGG    3149
             3370         339341           1130
3150 GGTTGTCTTGGAAACAGGGTCCTCTGACTTCCTCATGGGGGCTGCTCATACCCCCCTCCT    3209
             3430          3450           3470
3210 GGTGGATGTGTGTGTTTATTATGTGGAGTCACTACCACTTACTGCCTTATGACCTAGGAC    3269
             3490          3510           3530
3270 TGATGCTGTGGGGTGCTGGTGGAGCAGCTGATGTCGTGTTTACAGAGCAAGGCTTCCCTG    3329
             3550          3570           3590
3330 TCTCCCACGGGGAGGGGCTCGGGCCTCTAGTCAGACATTCCTGCAGAGGGTCGGTGGAGG    3389
             3610          3630           3650
3390 GTCATTCACCTGCCCCTGCAGCAAGCAAAAGTTGTCTGTGGTGCCATTTGATTCCCTGAC    3449
             3670          3690           3710
3450 ACTGCCCCTGCTTGAATTGATTCCGAAGGGTAGGGTGGGAAGGTGAGCAAAGGAGCAGAA    3509
             3730          3750           3770
3510 ACAAGGAATCAAGACCCAGAATGTAGGTGCCACTGCCTCCTATGTTTACAGGATCCTCCG    3560
             3790          3810           3830
3570 TGGCCCTAGGCACCTGGGCTGCAGGAAGTGACTCCGTTCCACTCCTCCTTTATTCCCTTA    3629
             3850          3870           3890
3630 AAAAGGGAAAAATGACTGTTACGACCCTGTTCACAAAACTCTTACTTTTGCTATTTTGTC    3689
             3910          3930           3950
3690 TGCTGTCCAGAACTGAAGACTTTAAAATTTTGTTACTGTTTACAAGTCCAGATTCACAAA    3749
             3970          3990           4010
3750 ATGTTTTTACTTTGTTTACAACTCAAAACTTTGAGTTTTACACTTTGTTTACAGTAGATA    3809
             4030          4060           4070
3810 ATTTTTTTTCCTTTGTTTCCAAGTGAAAGGTAGGGAAAGTGGGAGAGGGACTTGGAGGAC    3869
             4090          4110           4130
3870 CCACCTGTGAGGACCCTGACCTGGCCATCTTGAGGGGTTTTCTAACCCCCAGGTCTCCCA    3929
             4150          4170           4190
3930 GGCCGAAGGTCAGCCTTGAGTCCCGTTTAACAGCAGATCCAGAAGACCTTGAGAGTAGGC    3989
             4210          4230           4250
3990 GTCCTCTAACCACGGGGGAGAGTGGCTGTGCAGGGCTGGGGGTGGTCTGTGCAGACACC     4049
             4270          4290           4310
4050 TCCTCACCCACCACCCCATGCATACTCTTGGGAAGCAGCTTCCTGGGAGATTAGAAATTC    4109
             4330          4350           4370
4110 TACTTCCCTGACTGGAGCTAAATCCCACCAGCCAGGACCCAAACTCTCCTTACCGAGAAG    4169
             4390          4410           4430
4170 GACCCCAGCTCTTGAAGGGCTGAGTGGCCTGCTGGGGGTGGGAGGGTGTCTTTACTATGT    4229
             4450          4470           4490
4230 CCTAGGTTTTCGTAGATGCCCCTCTCTGGGGTTCCCCTCCTCCAGCCCAGCGGCCCTCTTT    4289
             4510          4530           4550
4290 CCTGTCTGTGTAAATTGTTCCGTGAAGCCGCGCTCTGTTTTGGGAATAAACTTCTATAGA    4349

4350 AAACAA                                                           4355
```

FIG. 1D

```
118  SRTGTFGVLMDASPRERLEGDLELLAVFTHVVVAV.......SVAALVLT        160
     :::..|. .:||:. : .|.: : . : || :      |:|.|. .
  7  GWSEPFPHYFDACGFDDYEPESGDQDYYYLSVKALYTVGYSTSLATLTTA         56

161  AAILLSLRSLKSNVRGIHANVAAALGVAELLFLL..........GIHRTH        200
     .|| ..:|.|..:.. || |: ...: : .: .::           :|
 57  MVILCRFRKLHCTRNFIHMNLFVSFMLRAISVFIKDWILYAEQDSSHCFV        106

201  NQLVCTAVAILLHYFFLSTFAWLFVQGLHLYRMQVEPRNVDRGAMRFYHA        250
     . : |.|| :::|| ..|.: |||::||.|: : ||.  .:|  : :|
107  STVECKAVMVFFHYCVVSNYFHLFIEGLYLFTLLVETFFPERRYFYWYTI        156

251  LGWGVPAVLLGLAVGL.......DPEGYGNPDFCWISVHEPLIWSFAGPV        293
     :|||.|.| :.: ..|        :. : .:.. |  |.:|:: |: ..
157  IGWGTPTVCVTVHAVLRLYFDDAGCWDMNDSTALWWVIKGPVVGSIMVNF        206

294  VLVIVM...............NGTMFLLAARTSCSTGQREAKKTSALTL         327
     ||.|.:                ::.::: .........:..||......: :.
207  VLFIGIIIILVQKLQSPDMGGNESSIYFSCVQKCYCKPQRAQQHSCKMSE        756

328  RSSFLLLLLVSASWLFGLLAVNHSILAF..........HYLHAGLCGLQG        367
     |.: || || |. :|:.|:::..::||           :. ||.::||
257  LSTITLRLARSTLLLIPLFGIHYTVFAFSPENVSKRERLVFELGLGSFQG        306

368  LAVLLLFCVLNADARAAWMPACLGRKAAP....EEARPAPGLPGAYNNT         413
     :.| :|:|.||::..|. .. ::|... :  :. |:|:..:: |..
307  FVVAVLYCFLNGEVQAEIKRKWRSWKVNRYFTMDFKHRHPSLASSGVNGG        356

414  ALFEESGLIRITLGASTVSSVSSARSG   440
     . :..  : . : |||.. .| |
357  TQLSILSKSSSHVRMSTVPADNLAT*G   383
```

FIG.3

HUMAN G-PROTEIN RECEPTOR HCEGH45

This application is a continuation of and claims benefit of 35 U.S.C. section 120 based on copending U.S. patent application Ser. No. 08/465,976, filed Jun. 6, 1995, now U.S. Pat. No. 5,869,632, and benefit of 35 U.S.C. section 119(e) based on copending U.S. Provisional Application Ser. No. 60/032,186, filed Dec. 2, 1996.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human 7-transmembrane receptor. The transmembrane receptor is a G-protein coupled receptor. More particularly, the 7-transmembrane receptor has been putatively identified as a human G-protein pituitary adenylate cyclase activating polypeptide (PACAP)-like receptor for amnesiac like neuropeptides, sometimes hereinafter referred to as "HCEGH45". The invention also relates to inhibiting the action of such polypeptides.

BACKGROUND OF THE INVENTION

It is well established that many medically significant biological process are mediated by proteins participating in signal transduction pathways that involve G-proteins and/or second messengers, e.g., cAMP (Lefkowitz, Nature, 351:353–354, 1991). Herein these proteins are referred to as proteins participating in pathways with G-proteins or PPG proteins. Some examples of these proteins include the GPC receptors, such as those foradrenergic agents and dopamine (Kobilka, B. K., et al., PNAS, 84:46–50 (1987); Kobilka, B. K., et al., Science, 238:650–656 (1987); Bunzow, J. R., et al., Nature, 336:783–787 (1988)), G-proteins themselves, effector proteins, e.g., phospholipase C, adenyl cyclase, and phosphodiesterase, and actuator proteins, e.g., protein kinase A and protein kinase C (Simon et al., Science, 252:802–8, (1991)).

For example, in one form of signal transduction, the effect of hormone binding is activation of an enzyme, adenylate cyclase, inside the cell. Enzyme activation by hormones is dependent on the presence of the nucleotide GTP, and GTP also influences hormone binding. A G-protein connects the hormone receptors to adenylate cyclase. G-protein was shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

A PACAP receptor protein purified from bovine cerebrum is disclosed in European Patent Application Publication Number 0 618 291 A2, the disclosure of which is incorporated by reference herein.

SUMMARY OF THE INVENTION

In accordance with one aspect of the present invention, there are provided novel polypeptides as well as fragments, analogs and derivatives thereof. The polypeptides of the present invention are of human origin.

In accordance with one aspect of the present invention, there are provided novel mature receptor polypeptides as well as biologically active and diagnostically or therapeutically useful fragments, analogs and derivatives thereof. The receptor polypeptides of the present invention are of human origin.

In accordance with another aspect of the present invention, there are provided isolated nucleic acid molecules encoding the receptor polypeptides of the present invention, including mRNAs, DNAs, cDNAs, genomic DNA as well as antisense analogs thereof and biologically active and diagnostically or therapeutically useful fragments thereof.

In accordance with a further aspect of the present invention, there are provided processes for producing such receptor polypeptides by recombinant techniques comprising culturing recombinant prokaryotic and/or eukaryotic host cells, containing nucleic acid sequences encoding the receptor polypeptides of the present invention, under conditions promoting expression of said polypeptides and subsequent recovery of said polypeptides.

In accordance with yet a further aspect of the present invention, there are provided antibodies against such receptor polypeptides.

In accordance with another aspect of the present invention there are provided methods of screening for compounds which bind to and activate or inhibit activation of the receptor polypeptides of the present invention.

In accordance with still another embodiment of the present invention there are provided processes of administering compounds to a host which bind to and activate the receptor polypeptide of the present invention which are useful in the prevention and/or treatment of amnesia and diseases related to nerve cell death, such as Alzheimer's disease, and other hyposecretory conditions.

In accordance with still another embodiment of the present invention there are provided processes of administering compounds to a host which bind to and inhibit activation of the receptor polypeptides of the present invention which are useful for preventing and/or treating PACAP hypersecretory conditions and for creating pharmacological amnesia.

In accordance with another aspect of the present invention there is provided a method of administering the receptor polypeptides of the present invention via gene therapy to treat conditions related to underexpression of the polypeptides or underexpression of a ligand to the receptor polypeptide.

In accordance with yet another aspect of the present invention, there are provided nucleic acid probes comprising nucleic acid molecules of sufficient length to specifically hybridize to the polynucleotide sequences of the present invention.

In accordance with still another aspect of the present invention, there are provided diagnostic assays for detecting diseases related to mutations in the nucleic acid sequences encoding such polypeptides and for detecting an altered level of the soluble form of the receptor polypeptides.

In accordance with yet a further aspect of the present invention, there are provided processes for utilizing such receptor polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 shows the cDNA sequence (SEQ ID NO:1) and the corresponding deduced amino acid sequence (SEQ ID NO:2) of the G-protein coupled receptor of the present invention. The standard one-letter abbreviation for amino acids is used. Sequencing was performed using a 373 Automated DNA Sequencer (Applied Biosystems, Inc.).

FIG. 3 illustrates an amino acid alignment of the G-protein coupled receptor of the present invention (SEQ ID NO:2) and rat PACAP-like receptor (SEQ ID NO:3).

DETAILED DESCRIPTION OF THE PREFERRED EMBODIMENTS

Figure 2:
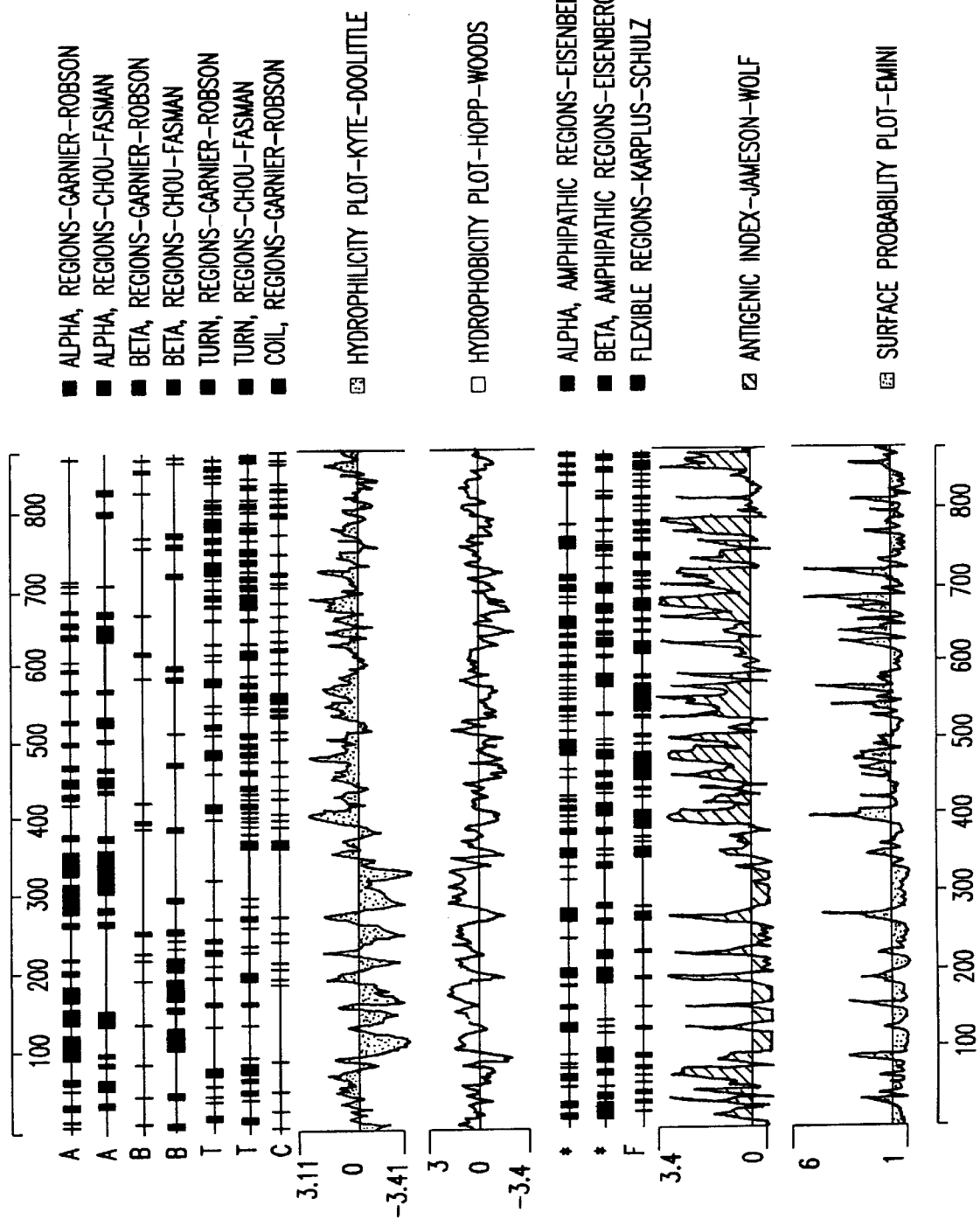
FIG. 2 is an illustration of the secondary structural features of the G-protein coupled receptor. The first 7 illustrations set forth the regions of the amino acid sequence which are alpha helices, beta sheets, turn regions or coiled regions. The boxed areas are the areas which correspond to the region indicated. The second set of figures illustrate areas of the amino acid sequence which are exposed to intracellular, cytoplasmic or are membrane-spanning. The hydrophilicity plot illustrates areas of the protein sequence which are the lipid bilayer of the membrane and are, therefore, hydrophobic, and areas outside the lipid bilayer membrane which are hydrophilic. The antigenic index corresponds to the hydrophilicity plot, since antigenic areas are areas outside the lipid bilayer membrane and are capable of binding antibodies. The surface probability plot further corresponds to the antigenic index and the hydrophilicity plot. The amphipathic plots show those regions of the protein sequences which are polar and non-polar. The flexible regions correspond to the second set of illustrations in the sense that flexible regions are those which are outside the membrane and inflexible regions are transmembrane regions.

In accordance with an aspect of the present invention, there is provided an isolated nucleic acid (polynucleotide) which encodes for the mature polypeptide having the deduced amino acid sequence of FIG. 1 or for the mature polypeptide encoded by the cDNA of the clone deposited as ATCC Deposit No. 97132 on Apr. 28, 1995. The ATCC (American Type Culture Collection) is located at 10801 University Boulevard, Manassas, Va. 20110-2209.

The polynucleotide of this invention was discovered in a cDNA library derived from human cerebellum tissue. It is structurally related to the G protein-coupled receptor family. It contains an open reading frame encoding a protein of 884 amino acid residues. The protein exhibits the highest degree of homology to rat PACAP-like receptor with 22.910% identity and 48.607% similarity.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 or that of the deposited clone or may be a different coding sequence which coding sequence, as a result of the redundancy or degeneracy of the genetic code, encodes the same mature polypeptide as the DNA of FIG. 1 or the deposited cDNA.

The polynucleotide which encodes for the mature polypeptide of FIG. 1 or for the mature polypeptide encoded by the deposited cDNA may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode fragments, analogs and derivatives of the polypeptide having the deduced amino acid sequence of FIG. 1 or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 or the same mature polypeptide encoded by the cDNA of the deposited clone as well as variants of such polynucleotides which variants encode a fragment, derivative or analog of the polypeptide of FIG. 1 or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode a soluble form of the receptor polypeptide which comprises the extracellular portion of the polypeptide minus the transmembrane portion and the intracellular portion.

The present invention also includes polynucleotides, wherein the coding sequence for the mature polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode a mature protein, or a protein having a prosequence or a protein having both a prosequence and a presequence (leader sequence).

The polynucleotides of the present invention may also have the coding sequence fused in frame to a marker sequence which allows for purification of the polypeptide of the present invention. The marker sequence may be, for example, a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson et al., *Cell*, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length HCEGH45 gene may be used as a hybridization probe for a cDNA library to isolate the full length gene and to isolate other genes which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete HCEGH45 gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a G-protein coupled receptor polypeptide which has the deduced amino acid sequence of FIG. 1 or which has the amino acid sequence encoded by the deposited cDNA, as well as fragments, analogs and derivatives of such polypeptide.

The terms "fragment," "derivative" and "analog" when referring to the polypeptide of FIG. 1 or that encoded by the deposited cDNA, means a polypeptide which either retains substantially the same biological function or activity as such polypeptide, i.e. functions as a G-protein coupled receptor, or retains the ability to bind the ligand or the receptor even though the polypeptide does not function as a G-protein coupled receptor, for example, a soluble form of the receptor. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIG. 1 or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID. NO:2 (in particular the mature polypeptide) as well as polypeptides which have at least 70% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 95% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the HCEGH45 genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Spodoptera Sf9; animal cells such as CHO, COS or Bowes melanoma; adenovirus plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis et al., Basic Methods in Molecular Biology, Elsevier, N.Y. (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual*, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The G-protein coupled receptor polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polynucleotides and polypeptides of the present invention may be employed as research reagents and materials for discovery of treatments and diagnostics to human disease.

The G-protein coupled receptor of the present invention may be employed in a process for screening for antagonists and/or agonists for the receptor.

In general, such screening procedures involve providing appropriate cells which express the receptor on the surface thereof. In particular, a polynucleotide encoding the receptor of the present invention is employed to transfect cells to thereby express the G-protein coupled receptor. Such transfection may be accomplished by procedures as hereinabove described.

One such screening procedure involves the use of the melanophores which are transfected to express the G-protein coupled receptor of the present invention. Such a screening technique is described in PCT WO 92/01810 published Feb. 6, 1992.

Thus, for example, such assay may be employed for screening for a receptor antagonist by contacting the melanophore cells which encode the G-protein coupled receptor with both the receptor ligand and a compound to be screened. Inhibition of the signal generated by the ligand indicates that a compound is a potential antagonist for the receptor, i.e., inhibits activation of the receptor.

The screen may be employed for determining an agonist by contacting such cells with compounds to be screened and determining whether such compound generates a signal, i.e., activates the receptor.

Other screening techniques include the use of cells which express the G-protein coupled receptor (for example, transfected CHO cells) in a system which measures extracellular pH changes caused by receptor activation, for example, as described in *Science*, 246:181–296 (October 1989). For example, potential agonists or antagonists may be contacted with a cell which expresses the G-protein coupled receptor and a second messenger response, e.g. signal transduction or pH changes, may be measured to determine whether the potential agonist or antagonist is effective.

Another such screening technique involves introducing RNA encoding the G-protein coupled receptor into xenopus oocytes to transiently express the receptor. The receptor oocytes may then be contacted in the case of antagonist screening with the receptor ligand and a compound to be screened, followed by detection of inhibition of a calcium signal.

Another screening technique involves expressing the G-protein coupled receptor in which the receptor is linked to a phospholipase C or D. As representative examples of such cells, there may be mentioned endothelial cells, smooth muscle cells, embryonic kidney cells, etc. The screening for an antagonist or agonist may be accomplished as hereinabove described by detecting activation of the receptor or inhibition of activation of the receptor from the phospholipase second signal.

Another method involves screening for antagonists by determining inhibition of binding of labeled ligand to cells which have the receptor on the surface thereof. Such a method involves transfecting a eukaryotic cell with DNA encoding the G-protein coupled receptor such that the cell expresses the receptor on its surface and contacting the cell with a potential antagonist in the presence of a labeled form of a known ligand. The ligand can be labeled, e.g., by radioactivity. The amount of labeled ligand bound to the receptors is measured, e.g., by measuring radioactivity of the receptors. If the potential antagonist binds to the receptor as determined by a reduction of labeled ligand which binds to the receptors, the binding of labeled ligand to the receptor is inhibited.

The present invention also provides a method for determining whether a ligand not known to be capable of binding to a G-protein coupled receptor can bind to such receptor which comprises contacting a mammalian cell which expresses a G-protein coupled receptor with the ligand under conditions permitting binding of ligands to the G-protein coupled receptor, detecting the presence of a ligand which binds to the receptor and thereby determining whether the ligand binds to the G-protein coupled receptor. The systems hereinabove described for determining agonists and/or antagonists may also be employed for determining ligands which bind to the receptor.

In general, antagonists for G-protein coupled receptors which are determined by screening procedures may be employed for a variety of therapeutic purposes. For example, such antagonists have been employed for treatment of hypertension, angina pectoris, myocardial infarction, ulcers, asthma, allergies, psychoses, depression, migraine, vomiting, and benign prostatic hypertrophy.

Agonists for G-protein coupled receptors are also useful for therapeutic purposes, such as the treatment of asthma, Parkinson's disease, acute heart failure, hypotension, urinary retention, and osteoporosis.

A potential antagonist is an antibody, or in some cases an oligonucleotide, which binds to the G-protein coupled receptor but does not elicit a second messenger response such that the activity of the G-protein coupled receptor is prevented.

Potential antagonists also include proteins which are closely related to the ligand of the G-protein coupled receptor, i.e. a fragment of the ligand, which have lost biological function and when binding to the G-protein coupled receptor, elicit no response.

A potential antagonist also includes an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.*, 6:3073 (1979); Cooney et al, *Science*, 241:456 (1988); and Dervan et al., *Science*, 251:1360 (1991)), thereby preventing transcription and the production of G-protein coupled receptor. The antisense RNA oligonucleotide hybridizes to the mRNA in vivo and blocks translation of the mRNA molecule into the G-protein coupled receptor (antisense—Okano, *J. Neurochem.*, 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of G-protein coupled receptor.

Another potential antagonist is a small molecule which binds to the G-protein coupled receptor, making it inaccessible to ligands such that normal biological activity is prevented. Examples of small molecules include but are not limited to small peptides or peptide-like molecules.

Potential antagonists also include a soluble form of a G-protein coupled receptor, e.g. a fragment of the receptor, which binds to the ligand and prevents the ligand from interacting with membrane bound G-protein coupled receptors.

The G-protein coupled receptor of the present invention has been putatively identified as a PACAP-like or secretin receptor. This identification has been made as a result of amino acid sequence homology.

The antagonists may be used to treat hypersecretory conditions and to create pharmacological amnesia or effect long-term memory. The antagonists may be employed in a composition with a pharmaceutically acceptable carrier, e.g., as hereinafter described.

The agonists identified by the screening method as described above, may be employed to treat hyposecretory conditions, to improve memory, to treat amnesia and prevent nerve cell death in neuropathy to prevent and/or treat diseases such as Alzheimer's disease.

The antagonists or agonists may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides or agonists or antagonists of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 $\mu$g/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

This invention also provides a method of detecting expression of a HCEGH45 receptor polypeptide of the present invention on the surface of a cell by detecting the presence of mRNA coding for the receptor which comprises obtaining total mRNA from the cell and contacting the mRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a HCEGH45 receptor polypeptide of the present invention, by low stringency cross hybridization, or by identifying receptors that interact with related natural or synthetic ligands and or elicit similar behaviors after genetic or pharmacological blockade of the neuropeptide receptor polypeptides of the present invention.

The HCEGH45 receptor polypeptides and antagonists or agonists which are polypeptides, may be employed in accordance with the present invention by expression of such polypeptides in vivo, which is often referred to as "gene therapy."

Thus, for example, cells from a patient may be engineered with a polynucleotide (DNA or RNA) encoding a is polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., calorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the HCEGH45 receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the HCEGH45 receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any HCEGH45 receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to HCEGH45 receptor proteins. Unattached reporter antibody is then washed out. Peroxidase substrates are then added to the dish and the amount of color developed in a given time period is a measurement of the amount of HCEGH45 receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in McKusick, *Mendelian Inheritance in Man* (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature*, 256:495–497, (1975)), the trioma technique, the human B-cell hybridoma technique (Kozbor et al., *Immunology Today* 4:72, (1983)), and the EBV-hybridoma technique to produce human monoclonal antibodies (Cole et al., in *Monoclonal Antibodies and Cancer Therapy*, Alan R. Liss, Inc., pp. 77–96, (1985)).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

EXAMPLES

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.*, 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis et al., Id., p. 146). Unless otherwise provided, ligation may be accomplished using known buffers and conditions with 10 units to T4 DNA ligase ("ligase") per 0.5 µg of approximately equimolar amounts of the DNA fragments to be ligated.

Unless otherwise stated, transformation was performed as described in the method of Graham and Van der Eb, *Virology*, 52:456–457 (1973).

Example 1
Expression of Recombinant HCEGH45 in COS-7 Cells

The expression of plasmid, HCEGH45-HA is derived from a vector pcDNAI/Amp (Invitrogen) containing: 1) SV40 origin of replication, 2) ampicillin resistance gene, 3) E.coli replication origin, 4) CMV promoter followed by a polylinker region, a SV40 intron and polyadenylation site. A DNA fragment encoding the entire HCEGH45 precursor and a HA tag fused in frame to its 3' end was cloned into the polylinker region of the vector, therefore, the recombinant protein expression is directed under the CMV promoter. The HA tag correspond to an epitope derived from the influenza hemagglutinin protein as previously described (Wilson et al., *Cell* 37:767, 1984). The infusion of HA tag to our target protein allows easy detection of the recombinant protein with an antibody that recognizes the HA epitope.

The plasmid construction strategy is described as follows:
The DNA sequence encoding HCEGH45, ATCC # 97132, was constructed by PCR was cloned using two primers: the 5' primer GGCTTCCTCGAATCCCGTCATGAACTCC (SEQ ID NO:4) contains an EcoRI site followed by 9 nucleotides of HCEGH45 coding sequence starting from the initiation codon; the 3' sequence GGGTTCTC-GAGCGGGCACTGCTCACAGAGGAGACG (SEQ ID NO:5) contains complementary sequences to an XhoI site, translation stop codon, HA tag and the last 11 nucleotides of the HCEGH45 coding sequence (not including the stop codon). Therefore, the PCR product contains an EcoRI site, HCEGH45 coding sequence, a translation termination stop codon and an XhoI site. The PCR amplified DNA fragment and the vector, pcDNAI/Amp, were digested with EcoRI and XhoI restriction enzyme and ligated. The ligation mixture was transformed into *E. coli* strain SURE (available from Stratagene Cloning Systems, 11099 North Torrey Pines Road, La Jolla, Calif. 92037) the transformed culture was plated on ampicillin media plates and resistant colonies were selected. Plasmid DNA was isolated from transformants and examined by restriction analysis for the presence of the correct fragment. For expression of the recombinant HCEGH45, COS-7 cells were transfected with the expression vector by DEAE-DEXTRAN method. (Sambrook et al., *Molecular Cloning: A Laboratory Manual*, Second Edition, Cold Spring Laboratory Press, (1989)). The expression of the HCEGH45-HA protein was detected by radiolabelling and immunoprecipitation method. (Harlow and Lane, *Antibodies: A Laboratory Manual*, Cold Spring Harbor Laboratory Press, (1988)). Cells were labelled for 8 hours with $^{35}$S-cysteine two days post transfection. Culture media were then collected and cells were lysed with detergent (RIPA buffer (150 mM NaCl, 1% NP-40, 0.1% SDS, 1% NP-40, 0.5% DOC, 50 mM Tris, pH 7.5). (Wilson et al., *Id.* 37:767 (1984)). Both cell lysate and culture media were precipitated with a HA specific monoclonal antibody. Proteins precipitated were analyzed on 15% SDS-PAGE gels.

Example 2

Cloning and Expression of HCEGH45 Using the Baculovirus Expression System

The DNA sequence encoding the full length HCEGH45 protein, ATCC # 97132, was amplified using PCR oligonucleotide primers corresponding to the 5' and 3' sequences of the gene:

The 5' primer has the sequence GTGCGTCCCGGGTTC-CTCAGACCGCCATC<u>ATG</u>AACTCC (SEQ ID NO:6) and contains a SmaI restriction enzyme site (in bold) followed by 17 nucleotides resembling an efficient signal for the initiation of translation in eukaryotic cells (Kozak, *J. Mol. Biol.* 196:947–950 (1987), and just behind the first 9 nucleotides of the HCEGH45 gene (the initiation codon for translation "ATG" is underlined).

The 3' primer has the sequence CGGGTACCA-GAGCGGGCA CTGCTCACAGAGGAGACG (SEQ ID NO:7) and contains the cleavage site for the restriction endonuclease Asp718 and 13 nucleotides complementary to the 3' non-translated sequence of the HCEGH45 gene. The amplified sequences were isolated from a 1% agarose gel using a commercially available kit ("Geneclean," BIO 101 Inc., La Jolla, Calif.). The fragment was then digested with the endonucleases SmaI and Asp718 and then purified as described above. This fragment is designated F2.

The vector pA2 (modification of pVL941 vector, discussed below) is used for the expression of the HCEGH45 protein using the baculovirus expression system (for review see: Summers and Smith, *A Manual of Methods for Baculovirus Vectors and Insect Cell Culture Procedures*, Texas Agricultural Experimental Station Bulletin No. 1555, 1987). This expression vector contains the strong polyhedrin promoter of the Autographa californica nuclear polyhedrosis virus (AcMNPV) followed by the recognition sites for the restriction endonucleases SmaI and Asp718. The polyadenylation site of the simian virus (SV)40 is used for efficient polyadenylation. For an easy selection of recombinant viruses the beta-galactosidase gene from *E.coli* is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow and Summers, *Virology*, 170:31–39 1989).

The plasmid was digested with the restriction enzymes SmaI and Asp718 and then dephosphorylated using calf intestinal phosphatase by procedures known in the art. The DNA was then isolated from a 1% agarose gel as described above. This vector DNA is designated V2.

Fragment F2 and the dephosphorylated plasmid V2 were ligated with T4 DNA ligase. *E.coli* HB101 cells were then transformed and bacteria identified that contained the plasmid (pBac-HCEGH45) with the HCEGH45 gene using the enzymes SmaI and Asp718. The sequence of the cloned fragment was confirmed by DNA sequencing.

5 μg of the plasmid pBac-HCEGH45 were co-transfected with 1.0 μg of a commercially available linearized baculovirus ("BaculoGold™ baculovirus DNA", Pharmingen, San Diego, Calif.) using the lipofection method (Felgner et al., *Proc. Natl. Acad. Sci. USA*, 84:7413–7417 (1987)).

1 μg of BaculoGold™ virus DNA and 5 μg of the plasmid pBac-HCEGH45 were mixed in a sterile well of a microtiter plate containing 50 μl of serum free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop wise to the Sf9 insect cells (ATCC CRL 1711) seeded in a 35 mm tissue culture plate with 1 ml Grace' medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum was added. The plate was put back into an incubator and cultivation continued at 27° C. for four days.

After four days the supernatant was collected and a plaque assay performed similar as described by Summers and Smith (supra). As a modification an agarose gel with "Blue Gal" (Life Technologies Inc., Gaithersburg) was used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution of the viruses was added to the cells, blue stained plaques were picked with the tip of an Eppendorf pipette. The agar containing the recombinant viruses was then resuspended in an Eppendorf tube containing 200 μl of Grace's medium. The agar was removed by a brief centrifugation and the supernatant containing the recombinant baculoviruses was used to infect Sf9 cells seeded in 35 mm dishes. Four days later the supernatants of these culture dishes were harvested and then stored at 4° C.

Sf9 cells were grown in Grace's medium supplemented with 10% heat-inactivated FBS. The cells were infected with the recombinant baculovirus V-HCEGH45 at a multiplicity of infection (MOI) of 2. Six hours later the medium was removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) were added. The cells were further incubated for 16 hours before they were harvested by centrifugation and the labelled proteins visualized by SDS-PAGE and autoradiography.

Example 3

Expression Pattern of HCEGH45 in Human Tissue

Northern blot analysis is carried out to examine the levels of expression of HCEGH45 in human tissues. Total cellular RNA samples are isolated with RNAzol™ B system (Biotecx Laboratories, Inc. 6023 South Loop East, Houston, Tex. 77033). About 10 μg of total RNA isolated from each human tissue specified is separated on 1% agarose gel and blotted onto a nylon filter. (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column. (5 Prime—3 Prime, Inc. 5603 Arapahoe Road, Boulder, Colo. 80303). The filter is then hybridized with radioactive labeled full length HCEGH45 gene at 1,000,000 cpm/ml in 0.5 M NaPO$_4$, pH 7.4 and 7%

SDS overnight at 65° C. After being washed twice at room temperature and twice at 60° C. with 0.5×SSC, 0.1% SDS, the filter is then exposed at −70° C. overnight with an intensifying screen. The message RNA for HCEGH45 is abundant in human cerebellum tissue.

Example 4

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., *DNA*, 7:219–25 (1988)) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer contains an EcoRI site and the 3' primer further includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polypeptide comprising:
   an amino acid sequence selected from the group consisting of:
   (a) the amino acid sequence shown as residues 1 to 884 of SEQ ID NO:2;
   (b) the amino acid sequence shown as residues 2 to 884 of SEQ ID NO:2;
   (c) at least 30 contiguous residues of SEQ ID NO:2; and
   (d) the amino acid sequence of an antigenic portion of SEQ ID NO:2.

2. The isolated polypeptide of claim 1 comprising the amino acid sequence of (a).

3. The isolated polypeptide of claim 1 comprising the amino acid sequence of (b).

4. The isolated polypeptide of claim 1 comprising the amino acid sequence of (c).

5. The isolated polypeptide of claim 1 comprising the amino acid sequence of (d).

6. An isolated polypeptide: having
   an amino acid sequence selected from the group consisting of:
   (a) the amino acid sequence shown as residues 1 to 884 of SEQ ID NO:2;
   (b) the amino acid sequence shown as residues 2 to 884 of SEQ ID NO:2;
   (c) at least 30 contiguous residues of SEQ ID NO:2; and
   (d) the amino acid sequence of an antigenic portion of SEQ ID NO:2.

7. The isolated polypeptide of claim 6 having the amino acid sequence of (a).

8. The isolated polypeptide of claim 6 having the amino acid sequence of (b).

9. The isolated polypeptide of claim 6 having the amino acid sequence of (c).

10. The isolated polypeptide of claim 6 having the amino acid sequence of (d).

11. The isolated polypeptide of claim 7 fused to a heterologous polypeptide.

12. The isolated polypeptide of claim 8 fused to a heterologous polypeptide.

13. The isolated polypeptide of claim 9 fused to a heterologous polypeptide.

14. The isolated polypeptide of claim 10 fused to a heterologous polypeptide.

15. An isolated polypeptide comprising:
    an amino acid sequence selected from the group consisting of:
    (a) the amino acid sequence of the complete protein encoded by the human cDNA contained in ATCC Deposit No. 97132;
    (b) the amino acid sequence of the mature protein encoded by the human cDNA contained in ATCC Deposit No. 97132;
    (c) at least 30 contiguous residues of the amino acid sequence of (a); and
    (d) the amino acid sequence of an antigenic portion of (a).

16. The isolated polypeptide of claim 15 comprising the amino acid sequence of (a).

17. The isolated polypeptide of claim 15 comprising the amino acid sequence of (b).

18. The isolated polypeptide of claim 15 comprising the amino acid sequence of (c).

19. The isolated polypeptide of claim 15 comprising the amino acid sequence of (d).

20. An isolated polypeptide having:
an amino acid sequence selected from the group consisting of:
   (a) the amino acid sequence of the complete protein encoded by the human cDNA contained in ATCC Deposit No. 97132;
   (b) the amino acid sequence of the mature protein encoded by the human cDNA contained in ATCC Deposit No. 97132;
   (c) at least 30 contiguous residues of the amino acid sequence of (a); and
   (d) the amino acid sequence of an antigenic portion of (a).

21. The isolated polypeptide of claim 20 having the amino acid sequence of (a).

22. The isolated polypeptide of claim 20 having the amino acid sequence of (b).

23. The isolated polypeptide of claim 20 having the amino acid sequence of (c).

24. The isolated polypeptide of claim 20 having the amino acid sequence of (d).

25. The isolated polypeptide of claim 21 fused to a heterologous polypeptide.

26. The isolated polypeptide of claim 22 fused to a heterologous polypeptide.

27. The isolated polypeptide of claim 23 fused to a heterologous polypeptide.

28. The isolated polypeptide of claim 24 fused to a heterologous polypeptide.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 4566 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 212..2863

(xi) SEQUENCE DESCRIPTION: SEQ ID NO:1:

```
GTCCCCACGG CCATCCCCAT CTAAGGTCCT GCCCACAAGC AGCAGCATAG AAAACTCCAC    60

CACCTCAAGT GTGGTCCCCC CACCAGCCCC GCCAGAGCCA GAGCCTGGGA TCTCCATTA   120

AATTCTCCTC GTTTACCGCA CCTTAGGGGG ACTGCTCCCT GCCCAGTTCC AGGCAGAAC   180

CCGAGGTGCC AGGCTTCCTC AGAACCCCGT C ATG AAC TCC CCG GTG GTC AGC     232
                                  Met Asn Ser Pro Val Val Ser
                                    1               5
```

```
GTG GCT GTG TTC CAC GGA CGC AAC TTC CTA AGG GGA ATC CTG GAG TCC  280
Val Ala Val Phe His Gly Arg Asn Phe Leu Arg Gly Ile Leu Glu Ser
         10                  15                  20

CCC ATC AGC CTA GAG TTT CGC CTG CTA CAG ACA GCG AAT CGG AGC AAG  328
Pro Ile Ser Leu Glu Phe Arg Leu Leu Gln Thr Ala Asn Arg Ser Lys
     25                  30                  35

GCG ATC TGT GTG CAG TGG GAC CCA CCT GGC CTG GCG GAG CAG CAT GGT  376
Ala Ile Cys Val Gln Trp Asp Pro Pro Gly Leu Ala Glu Gln His Gly
 40                  45                  50                  55

GTG TGG ACA GCA CGG GAC TGC GAG CTG GTG CAC AGG AAT GGG TCC CAC  424
Val Trp Thr Ala Arg Asp Cys Glu Leu Val His Arg Asn Gly Ser His
                 60                  65                  70

GCA CGG TGT CGC TGC AGC CGG ACA GGG ACC TTT GGG GTC CTC ATG GAT  472
Ala Arg Cys Arg Cys Ser Arg Thr Gly Thr Phe Gly Val Leu Met Asp
             75                  80                  85

GCC TCT CCC CGT GAG AGG CTG GAG GGC GAC CTG GAG CTG CTG GCT GTG  520
Ala Ser Pro Arg Glu Arg Leu Glu Gly Asp Leu Glu Leu Leu Ala Val
         90                  95                 100

TTC ACC CAC GTG GTC GTG GCT GTG TCT GTG GCT GCG CTG GTG CTG ACT  568
Phe Thr His Val Val Val Ala Val Ser Val Ala Ala Leu Val Leu Thr
     105                 110                 115

GCA GCC ATC CTG CTG AGC CTG CGC AGC CTC AAG TCC AAT GTG CGT GGG  616
Ala Ala Ile Leu Leu Ser Leu Arg Ser Leu Lys Ser Asn Val Arg Gly
120                 125                 130                 135

ATC CAT GCC AAT GTG GCA GCC GCC CTG GGG GTG GCA GAG CTC CTC TTC  664
Ile His Ala Asn Val Ala Ala Ala Leu Gly Val Ala Glu Leu Leu Phe
                 140                 145                 150

CTG CTG GGG ATT CAC AGG ACC CAC AAT CAG CTG GTG TGC ACT GCA GTC  712
Leu Leu Gly Ile His Arg Thr His Asn Gln Leu Val Cys Thr Ala Val
             155                 160                 165

GCC ATC CTC CTG CAC TAC TTC TTC CTC AGC ACC TTC GCG TGG CTC TTC  760
Ala Ile Leu Leu His Tyr Phe Phe Leu Ser Thr Phe Ala Trp Leu Phe
         170                 175                 180

GTG CAG GGG CTG CAC CTC TAC CGC ATG CAG GTT GAG CCA CGC AAC GTG  808
Val Gln Gly Leu His Leu Tyr Arg Met Gln Val Glu Pro Arg Asn Val
     185                 190                 195

GAC CGC GGC GCC ATG CGC TTC TAC CAT GCC CTG GGC TGG GGC GTC CCT  856
Asp Arg Gly Ala Met Arg Phe Tyr His Ala Leu Gly Trp Gly Val Pro
200                 205                 210                 215

GCT GTG CTG CTG GGC CTT GCT GTG GGC CTG GAC CCT GAG GGC TAT GGG  904
Ala Val Leu Leu Gly Leu Ala Val Gly Leu Asp Pro Glu Gly Tyr Gly
                 220                 225                 230

AAC CCT GAC TTC TGC TGG ATC TCA GTC CAC GAG CCC CTC ATC TGG AGC  952
Asn Pro Asp Phe Cys Trp Ile Ser Val His Glu Pro Leu Ile Trp Ser
             235                 240                 245

TTT GCT GGC CCT GTT GTC CTG GTC ATA GTG ATG AAC GGG ACC ATG TTT 1000
Phe Ala Gly Pro Val Val Leu Val Ile Val Met Asn Gly Thr Met Phe
         250                 255                 260

CTC CTC GCT GCC CGC ACA TCC TGC TCC ACA GGG CAG AGG GAG GCC AAG 1048
Leu Leu Ala Ala Arg Thr Ser Cys Ser Thr Gly Gln Arg Glu Ala Lys
     265                 270                 275

AAG ACC TCT GCA CTG ACC CTT CGC AGC TCC TTC CTG CTG CTT CTG 1096
Lys Thr Ser Ala Leu Thr Leu Arg Ser Ser Phe Leu Leu Leu Leu
280                 285                 290                 295

GTC AGT GCC TCC TGG CTC TTT GGG CTC CTG GCA GTC AAC CAC AGC ATC 1144
Val Ser Ala Ser Trp Leu Phe Gly Leu Leu Ala Val Asn His Ser Ile
                 300                 305                 310

CTA GCC TTC CAC TAC CTC CAT GCT GGA CTC TGC GGC CTC CAG GGC CTG 1192
Leu Ala Phe His Tyr Leu His Ala Gly Leu Cys Gly Leu Gln Gly Leu
             315                 320                 325
```

```
GCG GTG CTG CTG CTC TTC TGT GTC CTA AAT GCA GAT GCT CGG GCT GCC 1240
Ala Val Leu Leu Leu Phe Cys Val Leu Asn Ala Asp Ala Arg Ala Ala
        330                 335                 340

TGG ATG CCA GCC TGT CTG GGC AGG AAG GCA GCG CCT GAG GAG GCA AGG 1288
Trp Met Pro Ala Cys Leu Gly Arg Lys Ala Ala Pro Glu Glu Ala Arg
345                 350                 355

CCA GCA CCT GGG CTG GGA CCT GGG GCC TAC AAC AAC ACG GCT CTC TTT 1336
Pro Ala Pro Gly Leu Gly Pro Gly Ala Tyr Asn Asn Thr Ala Leu Phe
360                 365                 370                 375

GAG GAG AGT GGC CTC ATC CGC ATC ACT CTG GGC GCC TCC ACC GTC TCC 1384
Glu Glu Ser Gly Leu Ile Arg Ile Thr Leu Gly Ala Ser Thr Val Ser
            380                 385                 390

TCT GTG AGC AGT GCC CGC TCC GGC CGG ACC CAG GAC CAG GAC AGC CAG 1432
Ser Val Ser Ser Ala Arg Ser Gly Arg Thr Gln Asp Gln Asp Ser Gln
                395                 400                 405

CGG GGC CGC AGC TAC CTC AGG GAC AAT GTC CTG GTT CGA CAT GGC TCA 1480
Arg Gly Arg Ser Tyr Leu Arg Asp Asn Val Leu Val Arg His Gly Ser
            410                 415                 420

GCC GCT GAC CAC ACT GAC CAC AGC CTC CAG GCT CAT GCT GGC CCC ACT 1528
Ala Ala Asp His Thr Asp His Ser Leu Gln Ala His Ala Gly Pro Thr
                425                 430                 435

GAC CTG GAC GTG GAC ATG TTC CAT CGA GAT GCT GGC GCA GAC TCC GAC 1576
Asp Leu Asp Val Asp Met Phe His Arg Asp Ala Gly Ala Asp Ser Asp
440                 445                 450                 455

TCT GAC AGT GAC CTG TCC TTG GAG GAG GAG AGG AGT CTC TCC ATT CCA 1624
Ser Asp Ser Asp Leu Ser Leu Glu Glu Glu Arg Ser Leu Ser Ile Pro
            460                 465                 470

TCT TCA GAA AGC GAG GAC AAT GGC CGG ACG CGG GGG CGC TTC CAA CGG 1672
Ser Ser Glu Ser Glu Asp Asn Gly Arg Thr Arg Gly Arg Phe Gln Arg
                475                 480                 485

CCA CTC TGC CGA GCA GGC CAG AGT GAG AGG CTC CTC ACC CAC CCC AAA 1720
Pro Leu Cys Arg Ala Gly Gln Ser Glu Arg Leu Leu Thr His Pro Lys
            490                 495                 500

GAT GTG GAT GGC AAT GAC CTC CTG TCC TAC TGG CCA GCC CTG GGG GAG 1768
Asp Val Asp Gly Asn Asp Leu Leu Ser Tyr Trp Pro Ala Leu Gly Glu
505                 510                 515

TGC GAG GCA GCC CCC TGT GCT CTG CAG ACT TGG GGC TCT GAA AGG CGC 1816
Cys Glu Ala Ala Pro Cys Ala Leu Gln Thr Trp Gly Ser Glu Arg Arg
520                 525                 530                 535

CTG GGG CTG GAC ACC AGC AAG GAT GCA GCT AAC AAC AAC CAG CCA GAC 1864
Leu Gly Leu Asp Thr Ser Lys Asp Ala Ala Asn Asn Asn Gln Pro Asp
            540                 545                 550

CCG GCC CTG ACC AGT GGG GAT GAG ACT TCT CTG GGC CGG GCC CAG CGC 1912
Pro Ala Leu Thr Ser Gly Asp Glu Thr Ser Leu Gly Arg Ala Gln Arg
            555                 560                 565

CAG AGG AAA GGC ATC CTG AAG AAC CGG TTG CAA TAC CCA CTG GTG CCA 1960
Gln Arg Lys Gly Ile Leu Lys Asn Arg Leu Gln Tyr Pro Leu Val Pro
            570                 575                 580

CAG ACC CGA GGT GCC CCT GAG CTG TCC TGG TGC CGT GCA GCC ACC TTG 2008
Gln Thr Arg Gly Ala Pro Glu Leu Ser Trp Cys Arg Ala Ala Thr Leu
585                 590                 595

GGC CAC CGT GCT GTG CCA GCT GCC TCT TAC GGT CGC ATC TAT GCT GGC 2056
Gly His Arg Ala Val Pro Ala Ala Ser Tyr Gly Arg Ile Tyr Ala Gly
600                 605                 610                 615

GGG GGC ACG GGC AGC CTT TCA CAG CCA GCC AGC CGC TAC TCT TCT AGA 2104
Gly Gly Thr Gly Ser Leu Ser Gln Pro Ala Ser Arg Tyr Ser Ser Arg
            620                 625                 630

GAA CAG CTG GAC CTG CTC CTC CGG CGG CAA CTG AGC CGT GAG CGA CTA 2152
Glu Gln Leu Asp Leu Leu Leu Arg Arg Gln Leu Ser Arg Glu Arg Leu
            635                 640                 645
```

```
GAG GAA GCC CCT GCC CCT GTT CTA CGT CCC CTG AGC CGG CCA GGG TCC  2200
Glu Glu Ala Pro Ala Pro Val Leu Arg Pro Leu Ser Arg Pro Gly Ser
            650                 655                 660

CAG GAA TGC ATG GAT GCT GCA CCA GGC CGA CTG GAG CCC AAA GAT CGG  2248
Gln Glu Cys Met Asp Ala Ala Pro Gly Arg Leu Glu Pro Lys Asp Arg
665                 670                 675

GGC AGC ACC CTG CCA CGG AGG CAG CCA CCT CGG GAC TAC CCT GGC GCC  2296
Gly Ser Thr Leu Pro Arg Arg Gln Pro Pro Arg Asp Tyr Pro Gly Ala
680                 685                 690                 695

ATG GCT GGC CGC TTC GGG TCA CGG GAT GCG CTC GAC TTA GGG GCA CCT  2344
Met Ala Gly Arg Phe Gly Ser Arg Asp Ala Leu Asp Leu Gly Ala Pro
                700                 705                 710

CGA GAG TGG TTG AGC ACG CTG CCT CCG CCC CGC CGC ACC CGG GAC CTT  2392
Arg Glu Trp Leu Ser Thr Leu Pro Pro Pro Arg Arg Thr Arg Asp Leu
            715                 720                 725

GAC CAC AGC CCC CAC CTC TGC CCC TGT CTC CCC AGC GGC AAC TCT CAA  2440
Asp His Ser Pro His Leu Cys Pro Cys Leu Pro Ser Gly Asn Ser Gln
            730                 735                 740

GGG ACC CCC TCT TGC CAT CCC GGC CGC TGG ACT CTC TGT CTA GGA GCT  2488
Gly Thr Pro Ser Cys His Pro Gly Arg Trp Thr Leu Cys Leu Gly Ala
745                 750                 755

CGA ACT CTC GGG AGC AGC TGG ACC AGG TGC CTA GCC GGC ACC CCT CAC  2536
Arg Thr Leu Gly Ser Ser Trp Thr Arg Cys Leu Ala Gly Thr Pro His
760                 765                 770                 775

GAG AAG CCC TTG GGC CAC TCC CGC AGC TGC TCA GAG CTA GGG AGG ACT  2584
Glu Lys Pro Leu Gly His Ser Arg Ser Cys Ser Glu Leu Gly Arg Thr
                780                 785                 790

CGG TCA GTG GCC CCA GCC ATG GCC CCT CCA CAG AAC AGT TGG ACA TTC  2632
Arg Ser Val Ala Pro Ala Met Ala Pro Pro Gln Asn Ser Trp Thr Phe
            795                 800                 805

TTT CCT CCA TCC TTG CCT CTT TCA ACT CCT CGG CCC TCT CCT CTG TGC  2680
Phe Pro Pro Ser Leu Pro Leu Ser Thr Pro Arg Pro Ser Pro Leu Cys
            810                 815                 820

AAT CTT CAA GCA CAC CCT TGG GCC CTC ACA CCA CTG CCA CAC CTT CTG  2728
Asn Leu Gln Ala His Pro Trp Ala Leu Thr Pro Leu Pro His Leu Leu
825                 830                 835

CCA CAG CCT CTG TGC TTG GGC CCT CCA CGC CAC GTT CTG CCA CGT CTC  2776
Pro Gln Pro Leu Cys Leu Gly Pro Pro Arg His Val Leu Pro Arg Leu
840                 845                 850                 855

ACA GCA TCT CGG AGC TGT CGC CAG ACT CAG AAG TTC CCA GAA GTG AGG  2824
Thr Ala Ser Arg Ser Cys Arg Gln Thr Gln Lys Phe Pro Glu Val Arg
                860                 865                 870

GTC ACT CCT GAG GGG ATG ACG GCG TGG ACG AGG AAC AGC TGAGGGCGAC   2873
Val Thr Pro Glu Gly Met Thr Ala Trp Thr Arg Asn Ser
            875                 880

AGAGGATCTA GGCTAACAGG AGAGACTCCA GGAGTGGGGG CAGATCCCAA GGCAGCCT  2933

TGCTCCCCAG TGGTGGGTGC CCCAGCTCTA CCTGGTGTGG CAGGGCTGAG GCTCCATG  2993

CATCTGTGAG CATGCGTGTG ACAGGTGCAG AGACGGGGGA CTGGAGGGAG ACTTTTAT  3053

GTTTTGTACC TTTGTAACCA GAGAGATGCT TATGTTATTT TTCAGCTTTT CTGTCTCC  3113

GGGGGTTTGA GCCTGGCTGG GAGGGGGAGG GAGATAGAGG GAGAGATGCA GTTTGACC  3173

ATTTGGGTCC TGAGCAAACC CTATGCTCAT CTCTCTCTCC TTCCTGGGGT GGACTCAG  3233

GGGTGGGACA CATGCCTTCC TCCCCCTATT CCACCCCCAA GTTGATCTGA GTATCGTC  3293

GGGCCCAAGT ACAGAATTGT TCTTTGCTTT TTATTGAATG CTCCAAAGGC CAAACTTC  3353

GGGCTGGGGT TGTCTTGGAA ACAGGGTCCT CTGACTTCCT CATGGGGGCT GCTCATAC  3413

CCCTCCTGGT GGATGTGTGT GTTTATTATG TGGAGTCACT ACCACTTACT GCCTTATG  3473
```

```
CTAGGACTGA TGCTGTGGGG TGCTGGTGGA GCAGCTGATG TCGTGTTTAC AGAGCAAG    3533

TTCCCTGTCT CCCACGGGGA GGGGCTCGGG CCTCTAGTCA GACATTCCTG CAGAGGGT    3593

GTGGAGGGTC ATTCACCTGC CCCTGCAGCA AGCAAAAGTT GTCTGTGGTG CCATTTGA    3653

CCCTGACACT GCCCCTGCTT GAATTGATTC CGAAGGGTAG GGTGGGAAGG TGAGCAAA    3713

AGCAGAAACA AGGAATCAAG ACCCAGAATG TAGGTGCCAC TGCCTCCTAT GTTTACAG    3773

TCCTCCGTGG CCCTAGGCAC CTGGGCTGCA GGAAGTGACT CCGTTCCACT CCTCCTTT    3833

TCCCTTAAAA AGGGAAAAAT GACTGTTACG ACCCTGTTCA CAAAACTCTT ACTTTTGC    3893

TTTTGTCTGC TGTCCAGAAC TGAAGACTTT AAAATTTTGT TACTGTTTAC AAGTCCAG    3953

TCACAAAATG TTTTTACTTT GTTTACAACT CAAAACTTTG AGTTTTACAC TTTGTTTA    4013

GTAGATAATT TTTTTTCCTT TGTTTCCAAG TGAAAGGTAG GGAAAGTGGG AGAGGGAC    4073

GGAGGACCCA CCTGTGAGGA CCCTGACCTG GCCATCTTGA GGGGTTTTCT AACCCCCA    4133

TCTCCCAGGC CGAAGGTCAG CCTTGAGTCC CGTTTAACAG CAGATCCAGA AGACCTTG    4193

AGTAGGCGTC CTCTAACCAC GGGGGAGAGT GGCTGTGCAG GGCTGGGGGG TGGTCTGT    4253

AGACACCTCC TCACCCACCA CCCCATGCAT ACTCTTGGGA AGCAGCTTCC TGGGAGAT    4313

GAAATTCTAC TTCCCTGACT GGAGCTAAAT CCCACCAGCC AGGACCCAAA CTCTCCTT    4373

CGAGAAGGAC CCCAGCTCTT GAAGGGCTGA GTGGCCTGCT GGGGGTGGGA GGGTGTCT    4433

ACTATGTCCT AGGTTTCGTA GATGCCCCTC TCTGGGGTTC CCCTCCTCCA GCCCAGCG    4493

CCTCTTTCCT GTCTGTGTAA ATTGTTCCGT GAAGCCGCGC TCTGTTTTGG GAATAAAC    4553

CTATAGAAAA CAA                                                    4566
```

(2) INFORMATION FOR SEQ ID NO:2:

(i) SEQUENCE CHARACTERISTICS:
        (A) LENGTH: 884 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asn Ser Pro Val Val Ser Val Ala Val Phe His Gly Arg Asn Phe
 1               5                  10                  15

Leu Arg Gly Ile Leu Glu Ser Pro Ile Ser Leu Glu Phe Arg Leu Leu
            20                  25                  30

Gln Thr Ala Asn Arg Ser Lys Ala Ile Cys Val Gln Trp Asp Pro Pro
        35                  40                  45

Gly Leu Ala Glu Gln His Gly Val Trp Thr Ala Arg Asp Cys Glu Leu
    50                  55                  60

Val His Arg Asn Gly Ser His Ala Arg Cys Arg Cys Ser Arg Thr Gly
65                  70                  75                  80

Thr Phe Gly Val Leu Met Asp Ala Ser Pro Arg Glu Arg Leu Glu Gly
                85                  90                  95

Asp Leu Glu Leu Leu Ala Val Phe Thr His Val Val Ala Val
            100                 105                 110

Val Ala Ala Leu Val Leu Thr Ala Ala Ile Leu Leu Ser Leu Arg Ser
            115                 120                 125

Leu Lys Ser Asn Val Arg Gly Ile His Ala Asn Val Ala Ala Leu
        130                 135                 140

Gly Val Ala Glu Leu Leu Phe Leu Leu Gly Ile His Arg Thr His Asn
145                 150                 155                 160
```

-continued

```
Gln Leu Val Cys Thr Ala Val Ala Ile Leu Leu His Tyr Phe Phe Leu
                165                 170                 175

Ser Thr Phe Ala Trp Leu Phe Val Gln Gly Leu His Leu Tyr Arg Met
            180                 185                 190

Gln Val Glu Pro Arg Asn Val Asp Arg Gly Ala Met Arg Phe Tyr His
        195                 200                 205

Ala Leu Gly Trp Gly Val Pro Ala Val Leu Leu Gly Leu Ala Val Gly
    210                 215                 220

Leu Asp Pro Glu Gly Tyr Gly Asn Pro Asp Phe Cys Trp Ile Ser Val
225                 230                 235                 240

His Glu Pro Leu Ile Trp Ser Phe Ala Gly Pro Val Leu Val Ile
                245                 250                 255

Val Met Asn Gly Thr Met Phe Leu Leu Ala Ala Arg Thr Ser Cys Ser
            260                 265                 270

Thr Gly Gln Arg Glu Ala Lys Lys Thr Ser Ala Leu Thr Leu Arg Ser
        275                 280                 285

Ser Phe Leu Leu Leu Leu Val Ser Ala Ser Trp Leu Phe Gly Leu
    290                 295                 300

Leu Ala Val Asn His Ser Ile Leu Ala Phe His Tyr Leu His Ala Gly
305                 310                 315                 320

Leu Cys Gly Leu Gln Gly Leu Ala Val Leu Leu Phe Cys Val Leu
                325                 330                 335

Asn Ala Asp Ala Arg Ala Ala Trp Met Pro Ala Cys Leu Gly Arg Lys
            340                 345                 350

Ala Ala Pro Glu Glu Ala Arg Pro Ala Pro Gly Leu Gly Pro Gly Ala
        355                 360                 365

Tyr Asn Asn Thr Ala Leu Phe Glu Glu Ser Gly Leu Ile Arg Ile Thr
    370                 375                 380

Leu Gly Ala Ser Thr Val Ser Ser Val Ser Ser Ala Arg Ser Gly Arg
385                 390                 395                 400

Thr Gln Asp Gln Asp Ser Gln Arg Gly Arg Ser Tyr Leu Arg Asp Asn
                405                 410                 415

Val Leu Val Arg His Gly Ser Ala Ala Asp His Thr Asp His Ser Leu
            420                 425                 430

Gln Ala His Ala Gly Pro Thr Asp Leu Asp Val Asp Met Phe His Arg
        435                 440                 445

Asp Ala Gly Ala Asp Ser Asp Ser Asp Ser Asp Leu Ser Leu Glu Glu
    450                 455                 460

Glu Arg Ser Leu Ser Ile Pro Ser Ser Glu Ser Glu Asp Asn Gly Arg
465                 470                 475                 480

Thr Arg Gly Arg Phe Gln Arg Pro Leu Cys Arg Ala Gly Gln Ser Glu
                485                 490                 495

Arg Leu Leu Thr His Pro Lys Asp Val Asp Gly Asn Asp Leu Leu Ser
            500                 505                 510

Tyr Trp Pro Ala Leu Gly Glu Cys Glu Ala Ala Pro Cys Ala Leu Gln
        515                 520                 525

Thr Trp Gly Ser Glu Arg Arg Leu Gly Leu Asp Thr Ser Lys Asp Ala
    530                 535                 540

Ala Asn Asn Asn Gln Pro Asp Pro Ala Leu Thr Ser Gly Asp Glu Thr
545                 550                 555                 560

Ser Leu Gly Arg Ala Gln Arg Gln Arg Lys Gly Ile Leu Lys Asn Arg
                565                 570                 575

Leu Gln Tyr Pro Leu Val Pro Gln Thr Arg Gly Ala Pro Glu Leu Ser
            580                 585                 590
```

```
Trp Cys Arg Ala Ala Thr Leu Gly His Arg Ala Val Pro Ala Ala Ser
        595                 600                 605

Tyr Gly Arg Ile Tyr Ala Gly Gly Thr Gly Ser Leu Ser Gln Pro
        610                 615                 620

Ala Ser Arg Tyr Ser Ser Arg Glu Gln Leu Asp Leu Leu Arg Arg
625                 630                 635                 640

Gln Leu Ser Arg Glu Arg Leu Glu Glu Ala Pro Ala Pro Val Leu Arg
                    645                 650                 655

Pro Leu Ser Arg Pro Gly Ser Gln Glu Cys Met Asp Ala Ala Pro Gly
                    660                 665                 670

Arg Leu Glu Pro Lys Asp Arg Gly Ser Thr Leu Pro Arg Arg Gln Pro
        675                 680                 685

Pro Arg Asp Tyr Pro Gly Ala Met Ala Gly Arg Phe Gly Ser Arg Asp
        690                 695                 700

Ala Leu Asp Leu Gly Ala Pro Arg Glu Trp Leu Ser Thr Leu Pro Pro
705                 710                 715                 720

Pro Arg Arg Thr Arg Asp Leu Asp His Ser Pro His Leu Cys Pro Cys
                    725                 730                 735

Leu Pro Ser Gly Asn Ser Gln Gly Thr Pro Ser Cys His Pro Gly Arg
                    740                 745                 750

Trp Thr Leu Cys Leu Gly Ala Arg Thr Leu Gly Ser Ser Trp Thr Arg
        755                 760                 765

Cys Leu Ala Gly Thr Pro His Glu Lys Pro Leu Gly His Ser Arg Ser
        770                 775                 780

Cys Ser Glu Leu Gly Arg Thr Arg Ser Val Ala Pro Ala Met Ala Pro
785                 790                 795                 800

Pro Gln Asn Ser Trp Thr Phe Phe Pro Pro Ser Leu Pro Leu Ser Thr
                    805                 810                 815

Pro Arg Pro Ser Pro Leu Cys Asn Leu Gln Ala His Pro Trp Ala Leu
                    820                 825                 830

Thr Pro Leu Pro His Leu Leu Pro Gln Pro Leu Cys Leu Gly Pro Pro
        835                 840                 845

Arg His Val Leu Pro Arg Leu Thr Ala Ser Arg Ser Cys Arg Gln Thr
        850                 855                 860

Gln Lys Phe Pro Glu Val Arg Val Thr Pro Glu Gly Met Thr Ala Trp
865                 870                 875                 880

Thr Arg Asn Ser
```

(2) INFORMATION FOR SEQ ID NO:3:

(i) SEQUENCE CHARACTERISTICS:
        (A) LENGTH: 376 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Gly Trp Ser Glu Pro Phe Pro His Tyr Phe Asp Ala Cys Gly Phe Asp
1               5                   10                  15

Asp Tyr Glu Pro Glu Ser Gly Asp Gln Asp Tyr Tyr Tyr Leu Ser Val
                20                  25                  30

Lys Ala Leu Tyr Thr Val Gly Tyr Ser Thr Ser Leu Ala Thr Leu Thr
            35                  40                  45

Thr Ala Met Val Ile Leu Cys Arg Phe Arg Lys Leu His Cys Thr Arg
```

|   |   |   |   |   | 50 |   |   |   |   | 55 |   |   |   |   | 60 |   |   |
|---|---|---|---|---|---|---|---|---|---|---|---|---|---|---|---|---|---|

Asn Phe Ile His Met Asn Leu Phe Val Ser Phe Met Leu Arg Ala Ile
65                  70                  75                  80

Ser Val Phe Ile Lys Asp Trp Ile Leu Tyr Ala Glu Gln Asp Ser Ser
                85                  90                  95

His Cys Phe Val Ser Thr Glu Val Cys Lys Ala Val Met Val Phe Phe
                100                 105                 110

His Tyr Cys Val Val Ser Asn Tyr Phe Trp Leu Phe Ile Glu Gly Leu
                115                 120                 125

Tyr Leu Phe Thr Leu Leu Val Glu Thr Phe Phe Pro Glu Arg Arg Tyr
            130                 135                 140

Phe Tyr Trp Tyr Thr Ile Ile Gly Trp Gly Thr Pro Thr Val Cys Val
145                 150                 155                 160

Thr Val Trp Ala Val Leu Arg Leu Tyr Phe Asp Asp Ala Gly Cys Trp
                165                 170                 175

Asp Met Asn Asp Ser Thr Ala Leu Trp Trp Val Ile Lys Gly Pro Val
                180                 185                 190

Val Gly Ser Ile Met Val Asn Phe Val Leu Phe Ile Gly Ile Ile Ile
            195                 200                 205

Ile Leu Val Gln Lys Leu Gln Ser Pro Asp Met Gly Gly Asn Glu Ser
210                 215                 220

Ser Ile Tyr Phe Ser Cys Val Gln Lys Cys Tyr Cys Lys Pro Gln Arg
225                 230                 235                 240

Ala Gln Gln His Ser Cys Lys Met Ser Glu Leu Ser Thr Ile Thr Leu
                245                 250                 255

Arg Leu Ala Arg Ser Thr Leu Leu Leu Ile Pro Leu Phe Gly Ile His
                260                 265                 270

Tyr Thr Val Phe Ala Phe Ser Pro Glu Asn Val Ser Lys Arg Glu Arg
            275                 280                 285

Leu Val Phe Glu Leu Gly Leu Gly Ser Phe Gln Gly Phe Val Val Ala
        290                 295                 300

Val Leu Tyr Cys Phe Leu Asn Gly Glu Val Gln Ala Glu Ile Lys Arg
305                 310                 315                 320

Lys Trp Arg Ser Trp Lys Val Asn Arg Tyr Phe Thr Met Asp Phe Lys
                325                 330                 335

His Arg His Pro Ser Leu Ala Ser Ser Gly Val Asn Gly Gly Thr Gln
            340                 345                 350

Leu Ser Ile Leu Ser Lys Ser Ser Ser His Val Arg Met Ser Thr Val
        355                 360                 365

Pro Ala Asp Asn Leu Ala Thr Gly
370                 375

(2) INFORMATION FOR SEQ ID NO:4:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGCTTCCTCG AATCCCGTCA TGAACTCC                                                    28

(2) INFORMATION FOR SEQ ID NO:5:

-continued

```
    (i) SEQUENCE CHARACTERISTICS:
         (A) LENGTH: 35 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:5:

GGGTTCTCGA GCGGGCACTG CTCACAGAGG AGACG                              35

(2) INFORMATION FOR SEQ ID NO:6:

(i) SEQUENCE CHARACTERISTICS:
         (A) LENGTH: 38 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:6:

GTGCGTCCCG GGTTCCTCAG ACCGCCATCA TGAACTCC                           38

(2) INFORMATION FOR SEQ ID NO:7:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:7:

CGGGTACCAG AGCGGGCACT GCTCACAGAG GAGACG                             36
```